United States Patent [19]
Yamaguchi et al.

[11] Patent Number: 5,644,026
[45] Date of Patent: Jul. 1, 1997

[54] EPITAXIN, A CELL MOTILITY FACTOR

[75] Inventors: Yu Yamaguchi; Motoyuki Shimonaka, both of San Diego, Calif.

[73] Assignee: La Jolla Cancer Research Foundation, Ja Jolla, Calif.

[21] Appl. No.: 237,280

[22] Filed: May 3, 1994

[51] Int. Cl.$^6$ .................................................. C07K 14/00
[52] U.S. Cl. ........................... 530/326; 530/325; 530/324
[58] Field of Search ................................... 530/326, 324, 530/325; 514/13

[56] References Cited

U.S. PATENT DOCUMENTS

| | | | |
|---|---|---|---|
| 5,206,023 | 4/1993 | Hunziker | 424/423 |
| 5,497,543 | 9/1995 | Stracke et al. | 530/326 |

OTHER PUBLICATIONS

Watanabe, Hideomi et al., "Purification of Human Tumor Cell Autocrine Motility Factor and Molecular Cloning of Its Receptor. " *J. Biol. Chem.* 206:13442–13448 (1991).

"Inhibition of Lung Metastasis by Synthetic and Recombinant Fragenents of Human Fibronectin with Functional Domains."*Jpn. J. Cancer Res.* 81:1003–1011 (1990).

Chan, Andrew M. -L. et al., "Identification of a Competitive HGF Antagonist Encoded by an Alternative Transcript." *Science.* 254:2382–2384 (1991).

Stocker, Michael and Gherardi, Ermanno, "Regulation of Cell Movement: the Motogenic Cytokines." *Biochim. Biophys. Acta.* 1072:81–102 (1991).

Stoker, Michael et al., "Scatter Factor is a Fibroblast--derived Modulator of Epithelial Cell Mobility." *Nature.* 327:239–242 (1987).

Weidner, K. Michael et al., "Scatter Factor: Molecular Characteristics and effect on the Invasiveness of Epithelial Cells." *J. Cell. Biol.* 111:2097–2108 (1990).

Weidner, K. Michael, et al., "Evidence for the Identity of Human Scatter Factor and Human Hepatocyte Growth Factor." *Proc. Natl. Acad. Sci. USA* 88:7001–7005 (1991).

Naldini Luigi et al., "Scatter Factor and Hepatocyte Growth Factor are Indistinguishable Ligands for the *MET* Receptor." *EMBO J.* 10:2867–2878 (1991).

Gherardi, Ermanno et al., "Purification of Scatter Factor, a Fibroblast–derived Basic Protein that Modulates Epithelial Interactions and Movement." *Proc. Natl. Acad. Sci. USA* 86:5844–5848 (1989).

Nakamura, Toshikazu et al., "Purification and Characterization of a Growth Factor from Rat Platelets for Mature Parenchymal Hepatocytes in Primary Cultures." *Proc. Natl. Acad. USA* 83:6489–6493 (1986).

Liottam L.A. et al., "Tumor Cell Autocrine Motility Factor." *Proc. Natl. Acad. Sci. USA.* 83:3302–3306 (1986).

Koyama, N. et al., "Purificiation and Characterization of an Autocrine Migration Factor for Vascular Smooth Muscle Cell (SMC), SMC–derived Migration Factor." *J. Biol. Chem.* 268:13301–13308 (1993).

*Primary Examiner*—Cecilia J. Tsang
*Assistant Examiner*—Anish Gupta
*Attorney, Agent, or Firm*—Campbell & Flores LLP

[57] ABSTRACT

The present invention provides a substantially purified polypeptide, epitaxin, which is produced by fibroblasts and can stimulate migration of and DNA synthesis in a tumor cell. The invention also provides antibodies that are specifically reactive with epitaxin and cell lines that produce such antibodies. The invention also provides an active fragment antagonist of ETX activity, which can reduce or inhibit at least one activity of ETX. The invention further provides a method for controlling tumor cell migration and a method for controlling DNA synthesis in a tumor cell, comprising contacting the tumor cell with a composition of the invention. The invention also provides a method of increasing the sensitivity of a tumor cell to a cancer therapeutic agent.

1 Claim, 7 Drawing Sheets

Number of migrated cells

Upper chamber (ng/ml)

| ETX | 0 | 3 | 10 | 30 |
|---|---|---|---|---|
| 0 | 3.3 ± 1.8 | 6.0 ± 2.1 | 7.3 ± 2.3 | 12.5 ± 2.8 |
| 3 | 13.7 ± 2.1 | 11.3 ± 2.9 | 12.0 ± 2.6 | 15.7 ± 2.5 |
| 10 | 26.4 ± 3.7 | 22.8 ± 3.8 | 21.2 ± 5.4 | 20.8 ± 4.8 |
| 30 | 53.4 ± 9.7 | 36.6 ± 9.8 | 43.4 ± 9.9 | 36.1 ± 2.1 |

Lower chamber (ng/ml)

```
1     Xaa-Xaa-Ala-Pro-Asn-Pro-Ala-Pro-Gly-Xaa-
11    (Gly)-Val-Glu-(Asp)-Leu-Gln-Gln-Gly-Gln-Glu-(Ala)
```

FIG. 7

EPITAXIN, A CELL MOTILITY FACTOR

This work was supported by grant CA 57366 awarded by the National Cancer Institute of the National Institutes of Health. The United States Government has certain rights in this invention.

BACKGROUND OF THE INVENTION

1. Field of the Invention

This invention relates generally to the field of protein biochemistry and more specifically to epitaxin, which is a cell motility factor.

2. Background Information

Cell migration is regulated by various extracellular signals at different molecular levels. Cell-substrate adhesion provides an anchorage that allows moving cells to derive traction and cell-cell adhesion and intercellular junctions act to restrict the movement of cells by binding them to neighboring cells. However, the cellular factors that signal a cell when and where to move only now are being identified.

Various cellular proteins such as cytokines can act as motility factors, which regulate cell migration. In general, these cell motility factors can direct particular cell types to a region of inflammation or an area of wound healing. Normally, the migration of specific cell types is tightly regulated. However, various cancers are characterized, in part, by unregulated cell migration, which can result in tumor cell invasion and metastasis. The unregulated migration of tumor cells suggests that cell motility factors can have a significant role in tumor cell invasion and metastasis. Thus, the identification of cell motility factors that act on specific types of tumor cells can provide a means to intervene in the process of tumor cell invasion and metastasis.

Several cell motility factors recently have been described. However, with the exception of scatter factor (hepatocyte growth factor; SF/HGF), the motility factors thus far identified primarily direct the migration of non-epithelial cell types. Unfortunately, nearly 90% of human malignant tumors arise from cells of epithelial origin.

Thus, there exists a need to identify motility factors that can control the migration of a wide range of tumor cell types, including tumor cells of epithelial origin and, therefore, are useful for reducing or inhibiting the invasiveness or metastatic potential of the tumor cells. The present invention satisfies this need and provides additional advantages as well.

SUMMARY OF THE INVENTION

The present invention provides a substantially purified polypeptide, epitaxin, which is produced by fibroblasts and can stimulate migration of and DNA synthesis in tumor cells. The invention also provides antibodies that are specifically reactive with epitaxin and cell lines that produce such antibodies. The invention also provides an active fragment antagonist of ETX activity, which can reduce or inhibit at least one activity of ETX. The invention further provides a method for controlling tumor cell migration and a method for controlling DNA synthesis in a tumor cell by contacting the tumor cell with a composition of the invention. The invention also provides a method of increasing the sensitivity of a tumor cell to a cancer therapeutic agent.

BRIEF DESCRIPTION OF THE FIGURES

FIGS. 1.A. to 1.C. Purification of Epitaxin by RP-HPLC.

A. Combined active fractions of epitaxin from hydrophobic interaction chromatography on phenyl-Sepharose were fractionated by reverse phase high performance liquid chromatography (RP-HPLC) using a Vydac C4 column (4.6×250 mm; preequilibrated with 0.1% TFA). Fractions were eluted using a linear acetonitrile gradient (10–60% in 100 min). HPLC-grade TFA and acetonitrile were purchased from J. T. Baker (Phillipsburg, N.J.) and Baxter (Muskegon, Mich.), respectively.

B. Active fractions from the RP-HPLC were reloaded on the same Vydac C4 column and eluted using a shallow gradient of acetonitrile (16–36% in 100 min). Fractionations were performed at a flow rate of 0.5 ml/min and 1 ml fractions were collected. Each fraction was assayed for epitaxin activity (bars).

C. Sodium dodecyl sulfate-polyacrylamide gel electrophoresis (SDS-PAGE) analysis of fractions collected from the second RP-HPLC column were examined using a 4–20% gradient gel under nonreducing condition. Positions of molecular weight standards (Pharmacia) are shown on the left. The 36 (kiloDalton) kDa band coincided with the elution pattern of the epitaxin activity (arrow).

FIGS. 2.A. and 2.B. SDS-PAGE of Purified Epitaxin and Recovery of Epitaxin from Gel Slices.

A. Purified epitaxin was subjected to SDS-PAGE on a 4–20% gradient gel (Novex) under nonreducing conditions and visualized by silver staining. Molecular weight standards (Pharmacia) are shown on the left of the gel.

B. An aliquot of purified epitaxin was concentrated, resolved in a 4–20% gradient gel under nonreducing conditions and electrophoretically transferred to a PVDF membrane. The membrane was cut into 12 slices and each slice was eluted with 40% acetonitrile at 37° C. for 3 hr, then with 40% acetonitrile/0.5% TFA at 50° C. for 30 min. Combined eluents were lyophilized in the presence of bovine serum albumin (BSA) and assayed for epitaxin activity using HepG2 cells. The numbers to the left of the graph indicate the estimated molecular weights corresponding to each border of the gel slices.

FIG. 3. Effects of Neutralizing Antibodies against SF/HGF and IL-6 on the Migration of HepG2 Cell Induced by Epitaxin. Epitaxin (ETX; 30 ng/ml), scatter factor/hepatocyte growth factor (SF/HGF; 30 ng/ml) or interleukin-6 (IL-6; 6000 units/ml) was mixed with polyclonal anti-human SF/HGF neutralizing antibodies (αHGF; 200 µg/ml), monoclonal anti-human IL-6 neutralizing antibodies (αIL-6; 200 µg/ml), polyclonal anti-human serum albumin (RαHSA; 200 µg/ml; Sigma, St. Louis Mo.) or monoclonal anti-HSA (MαHSA; 200 µg/ml; Sigma). Following incubation for 1 hr at 37° C., the mixtures were added to the lower chambers of the 48 well chemotaxis apparatus and migration was determined using HepG2 cells. Data represent the mean ±1 standard deviation (SD; n=3).

FIG. 6. Effects of Epitaxin and SF/HGF on the DNA Synthesis of HepG2 Cells. Confluent monolayers of HepG2 cells were grown in Corning 96-½ well tissue culture plates and treated for 24 hr with varying concentrations of ETX (●) or SF/HGF (Δ) diluted in α-MEM containing 1% fetal calf serum (FCS). Cells were pulsed with $^3$H-thymidine for 2 hr and incorporation into DNA was measured after precipitation with 10% trichloroacetic acid (TCA). The experiment was performed in duplicate and repeated twice with similar results.

DETAILED DESCRIPTION OF THE INVENTION

The present invention provides a substantially purified fibroblast-derived motility factor, epitaxin, that stimulates the migration of tumor cells, including tumor cells of epithelial cell origin but not tumor cells of fibroblast origin. As used herein, the term "substantially purified" means that the polypeptide is in a form that is essentially free of other biological molecules such as lipids, proteins or nucleic acids with which the polypeptide normally is associated in nature. A polypeptide produced using methods of recombinant DNA technology is an example of a substantially purified polypeptide as is a polypeptide that is purified using immunochemical methods or biochemical methods.

As used herein, the term "polypeptide" is used in its broadest sense to mean a sequence of amino acids and, therefore, is synonymous with the term "protein." The term "polypeptide" encompasses, for example, a core ETX polypeptide sequence, which contains no modified amino acids and can be produced using recombinant DNA methods, as well as a polypeptide containing modified amino acid sequences, including, for example, amino acids modified by carbohydrate, lipid or phosphate groups or other well known modifications that can occur in a naturally occurring polypeptide. For convenience, an active fragment of ETX, as described below, also is considered to be within the meaning of the term "polypeptide."

Figure 1A:
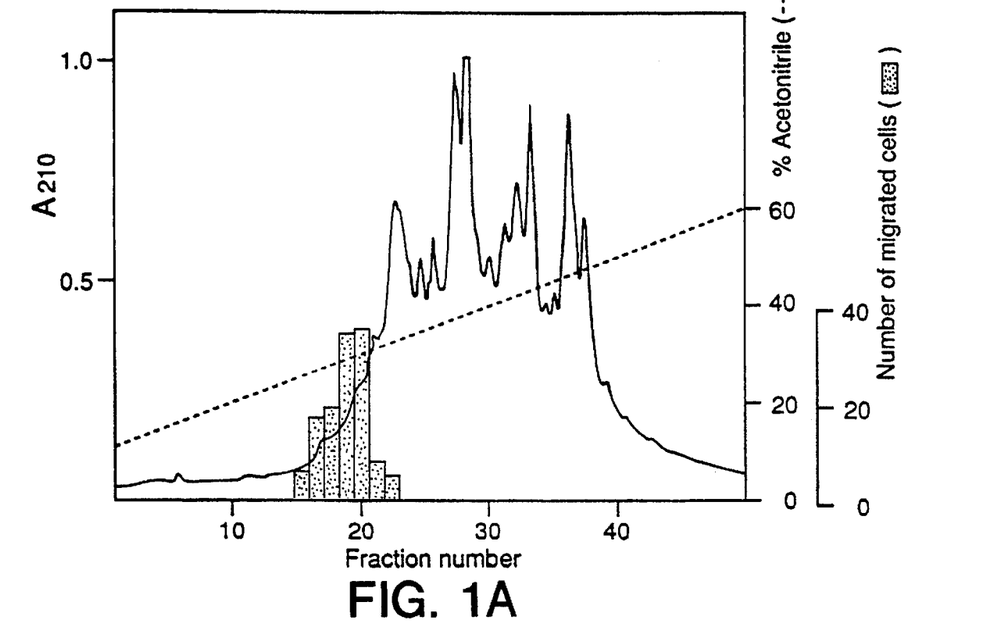
Figure 1B:
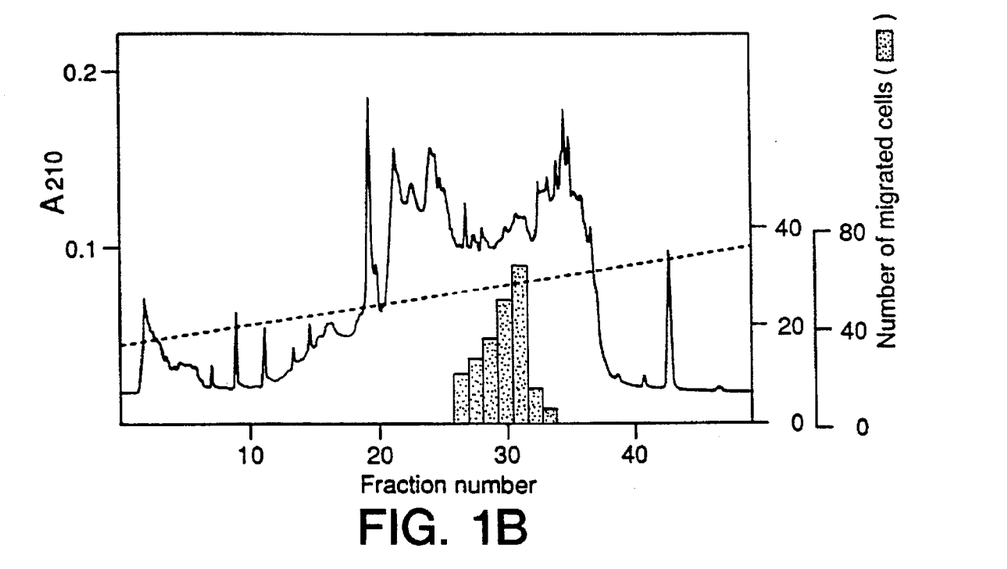
Figure 1C:
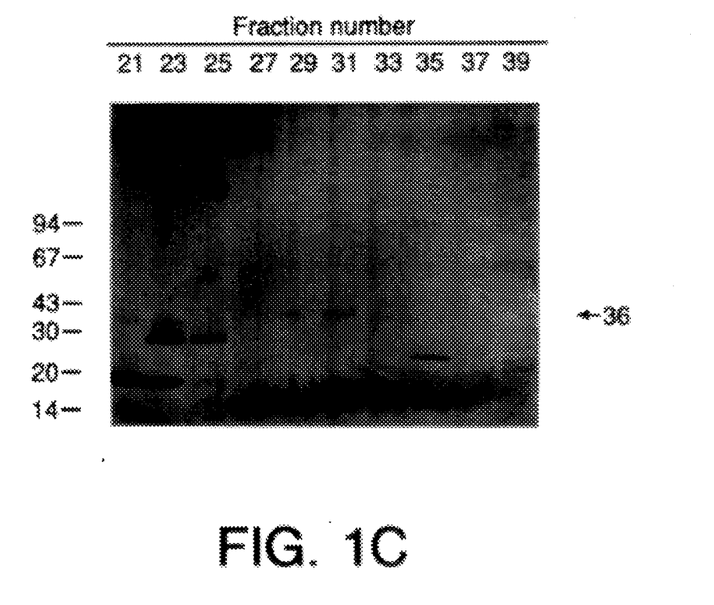

As disclosed herein, substantially purified ETX has an apparent molecular mass of about 36 kDa as determined by SDS-PAGE under nonreducing conditions (see FIG. 1.C.). In addition, ETX has characteristic functional activities, including the ability to induce or stimulate the migration of a tumor cell and to increase DNA synthesis in such a cell, provided the tumor cell is not derived from a fibroblast (Example II). As used herein, the terms "derived from a fibroblast (epithelial cell)" or "of fibroblast (epithelial) origin" refers to the class of normal cell-types into which the tumor cell can be classified. For example, an adenocarcinoma contains tumor cells that are of epithelial origin, whereas a sarcoma contains tumor cells derived from a fibroblast.

The terms "induce" and "stimulate" when referring to the action of ETX on cell migration are used interchangeably herein and mean that contact of a cell with ETX causes the cell to migrate at a greater level than the cell migrates in the absence of ETX. Methods for determining the level of cell migration are described below and shown, for example, in FIG. 5. Since the different functional activities of ETX can be mediated by different domains present in the ETX polypeptide, the invention also provides active fragments of ETX, which can mediate one or more functional activities associated with ETX.

Unless otherwise indicated, use of the term "epitaxin" or "ETX" includes the entire ETX polypeptide or a functionally equivalent polypeptide as well as active fragments thereof. For example, a functionally equivalent polypeptide can have an amino acid sequence that is similar to ETX but that contains amino acid substitutions or other modifications have been made in the polypeptide that do not substantially alter the ETX activity as disclosed herein. It is well recognized that various amino acids in a polypeptide can be replaced by other naturally- or non-naturally-occurring L- or D-amino acids having equivalent reactive side chains or by other chemical compounds without substantially changing the activity of the polypeptide. For example, a hydrophobic amino acid such as leucine can be replaced by another hydrophobic amino acid such as alanine without substantially changing the sequence or activity of an ETX polypeptide. In addition, the N-terminus or C-terminus or a reactive side chain of an amino acid can be modified, for example, by acetylation or amidation, without substantially changing the activity of an ETX polypeptide. Such functionally equivalent polypeptides can have advantageous properties including, for example, increased stability in vivo or in vitro. ETX polypeptides having such substitutions or modifications are considered to be within the meaning of the term "epitaxin" or "ETX" as used herein and, therefore, within the scope of the invention.

A polypeptide of the invention is characterized, in part, by having ETX activity. As used herein, the term "ETX activity" or "epitaxin activity" means that the polypeptide can stimulate cell motility or cell migratory activity or can increase DNA synthesis in a cell. For example, ETX activity stimulates the migration of tumor cells and, in particular, tumor cells that are de-differentiated (see Table II). Furthermore, ETX activity can stimulate migration of or increase DNA synthesis of various types of tumor cells, such as tumor cells of epithelial origin, but not tumor cells that are derived from fibroblasts.

As used herein, the term "active fragment" of ETX or of a functionally equivalent polypeptide means an amino acid sequence that is a portion of the entire ETX polypeptide, provided the amino acid sequence retains at least one characteristic activity of ETX as disclosed herein or, as described below, is antagonistic to at least one activity of ETX. For example, an active fragment of ETX can have cell motility activity and, therefore, can induce migration of tumor cells, including a tumor cell of epithelial origin but not a tumor cell derived from a fibroblast. An active fragment of ETX also can stimulate DNA synthesis in such a tumor cell and, as a result, can increase the level of cell proliferation. An active fragment of ETX also can be an amino acid sequence that is an immunogenic peptide, which can be used to obtain an anti-ETX antibody as described below. The N-terminal amino acid sequence of ETX (FIG. 7 SEQ ID NO:1 ), which is not homologous to any protein listed in the Brookhaven Protein DataBank (SWISS-PROT 27.0; PIR 38.0; SWISS-PROT update) and GenBank Release 79.0 (with update), is an example of an active fragment of ETX that can be used as an immunogen to obtain an anti-ETX antibody.

An active fragment of ETX also can be an antagonist of at least one activity that is characteristic of ETX. Similar antagonist activity has been described, for example, for a fragment of HGF (Chan et al., *Science* 254:2382–2384 (1991)). Thus, the invention also provides an active fragment antagonist of ETX activity, which is a portion of the ETX polypeptide that acts as an antagonist of at least one ETX activity.

It is further recognized that various other agents can be functional equivalents of ETX or active fragments thereof and, therefore, are considered within the broad meaning of the term "epitaxin" or "ETX." As used herein, the term "functional equivalent" means a chemical or biochemical agent that has at least one activity that is characteristic of ETX. For example, an anti-idiotypic antibody, which is raised against an anti-ETX antibody that can reduce or inhibit the cell migratory activity of ETX as discussed below, can have an activity of ETX such as the ability to stimulate cell migration. In addition, a chemical such as a drug, which has an activity that is characteristic of ETX, can mimic the activity of ETX as determined by routine screening assays such as the cell migration assay described herein. These and other functional equivalents of ETX are encompassed within the claimed invention.

Cell migration is regulated by various extracellular signals at different molecular levels (see Stoker and Gherardi, *Biochim. Biophys. Acta* 1072:81–102 (1991)). Cytokines, which can activate cell proliferation, were among the first cellular factors identified as regulating the migration of various cell types. Such cytokines include acidic and basic fibroblast growth factors (FGF; Valles et al., *Proc. Natl. Acad. Sci.*, USA 87:1124–1128 (1990); Moscatelli et al., *Proc. Natl. Acad. Sci.*, USA 83:2091–2095 (1986)), platelet-derived growth factor (PDGF; Grotendorst et al., *Proc. Natl. Acad. Sci.*, USA 78:3669–3672 (1981)), the insulin-like growth factors (IGF-1 and IGF-II; Stracke et al., *Biochem. Biophys. Res. Comm.* 153:1076–1083 (1988); El-Badry et al., *Cell Growth Diff.* 1:325–331 (1990)), a transforming growth factor (TGF-β; Postlethwaite et al., *J. Exp. Med.* 165:251–256 (1987)), a tumor necrosis factor (TNF-α; Rosen et al., *Canc. Res.* 51:5315–5321 (1991)) and interleukin-6 (IL-6; Tamm et al., *J. Exp. Med.* 170:1649–1669 (1989)). These cytokines originally were isolated as mitogenic factors and their effects on cell motility were observed as a secondary phenomenon (Stoker and Gherardi, supra, 1991).

A class of proteins, termed "motility factors," predominantly stimulate the migration of various types of cells (Stoker and Gherardi, supra, 1991)). Motility factors have been identified and isolated based on assay C systems that measure cell motility. For example, Yoshida et al., *Int. J. Canc.* 6:123–132 (1970), demonstrated that tumor cells produce and secrete an autocrine cell motility factor, which enhances chemotaxis of the producer cells.

Several motility factors have been purified. Autocrine motility factor (AMF) is a 55 kDa protein that was derived from melanoma and mammary carcinoma cell lines and stimulates chemotaxis of the producer cells (Liotta et al., *Proc. Natl. Acad. Sci.*, USA 83:3302–3306 (1986); Atnip et al., *Biochem. Biophys. Res. Comm.* 146:966–1002 (1987); Silletti et al., *Canc. Res.* 51:3507–3511 (1991)). Migration-stimulating factor (MSF) is a 77 kDa protein that is produced by human fetal fibroblasts and by fibroblasts in breast cancer patients and stimulates the migration of the producer cells into collagen matrix (Grey et al., *Proc. Natl. Acad. Sci.*, USA 86:2438–2442 (1989)). Autotaxin is a 125 kDa protein that, like AMF, stimulates the motility of melanoma cells in an autocrine fashion (Stracke et al., *J. Biol. Chem.* 267:2524–2529 (1992)). In addition, a 58 kDa autocrine motility factor for vascular smooth muscle cells (SDMF) has been described (Koyama et al., *J. Biol. Chem.* 268:13301–13308 (1993)). In comparison, scatter factor, which is the same as hepatocyte growth factor (SC/HGF), is a paracrine cell motility factor that is produced by fibroblasts and causes colonies of epithelial cells to scatter into single cells (Stoker et al., *Nature* 327:239–242 (1987); Weidner et al., *J. Cell Biol.* 111:2097–2108 (1990); Weidner et al., *Proc. Natl. Acad. Sci.*, USA 88:7001–7005 (1991); Naldini et al., *EMBO J.* 10:2867–2878 (1991)). The ability of cell motility factors to stimulate cell migration suggests these factors are involved in tumor cell invasion and metastasis (Hart et al., *Biochim. Biophys. Acta* 989:65–84 (1989); Liotta and Stetler-Stevenson, *Cancer Res.* (suppl) 51:5054s–5059s. (1991); Stoker and Gherardi, supra, 1991).

As disclosed herein, substantially purified epitaxin, which was obtained from human fibroblast conditioned medium by ammonium sulfate precipitation, hydrophobic interaction chromatography on phenyl-Sepharose and RP-HPLC, is a novel cell motility factor. ETX has the biological activity of inducing or stimulating migration of a tumor cell and of increasing DNA synthesis in such a cell. Substantially purified ETX migrated as a 36 kDa band on an SDS-PAGE under nonreducing conditions and the biological activity was recovered from the area in the gel coinciding with this band (see FIG. 2). ETX is shown, for example, to stimulate the motility of HepG2 cells, which are tumor cells of epithelial origin, at concentrations greater than 1 ng/ml with half maximal activity at 4.2 ng/ml (see FIG. 4). Based on these characteristics, ETX can be distinguished from other cell motility factors, as described below. ETX increases the motility of a wide variety of tumor cell lines, including lung carcinoma cells (A549), rat bladder tumor cells (NBT-II), breast ductal carcinoma cells (ZR-75-1) and de-differentiated hepatoma cells (C2) but not the various fibroblast cell lines examined (see Table II). Thus, ETX is a fibroblast-derived factor that affects the migration of a tumor cell, including a tumor cell of epithelial origin, but not a tumor cell that is derived from a fibroblast.

ETX is readily distinguishable from other cell motility factors that have been described. For example, autotaxin did not have any effect on the HepG2 cells. In addition, autotaxin has a greater molecular mass than ETX. Although AMF, MSF and SDMF were not examined directly here, ETX can be distinguished from these other cell motility factors based on differences in molecular mass, biochemical properties, target cell specificity and cellular source. Although SF/HGF has a similar effect on the motility of HepG2 cells, it is distinct from ETX for the following reasons. First, SF/HGF is a much larger molecular species than ETX. Active SF/HGF preparations isolated from various sources migrate as a single band of 62–75 kDa in nonreducing SDS-PAGE (Gherardi et al., *Proc. Natl. Acad. Sci.* USA 86:5844–5848 (1989); Weidner et al., supra, 1990; Naldini et al., supra, 1991)). A naturally occurring 28 kDa variant of HGF exists. However, the 28 kDa variant is an antagonist for HGF and does not have biological activity by itself (Chan et al., supra, 1991). Second, ETX has the characteristics of an acidic protein in that it binds to anion exchange column but not to heparin column (not shown). In contrast, both the active form of SF/HGF and the 28 kDa variant are basic heparin-binding proteins (Nakamura et al., *Proc. Natl. Acad. Sci.* USA 83:6489–6493 (1986); Gherardi et al., supra, 1989; Weidner et al., supra, 1990; Chan et al., supra, 1991). Finally, the antibody neutralizing experiments clearly demonstrate that, since anti-SF/HGF antibody did not inhibit ETX activity, the activity of ETX is not mediated by SF/HGF (see FIG. 3, αHGF). The biological activities of ETX and SF/HGF also can be distinguished. For example, SF/HGF and ETX have opposite effects on the growth of HepG2 cells (FIG. 6). Also, ETX does not scatter HepG2 or MDCK cells, while SF/HGF scatters both (see Example III). Thus, ETX is a novel cell motility factor as disclosed herein.

ETX has a target cell specificity toward relatively de-differentiated tumor cells (see Example III). In particular, mammalian cell lines derived from malignant tumors, including human lung carcinoma cells (A549), rat bladder tumor cells (NBT-II), human breast ductal carcinoma cells (ZR-75-1) and de-differentiated rat hepatoma cells (C2) responded to ETX, whereas normal canine MDCK cells did not. A similar tendency also was observed with a series of rat hepatoma cell lines in that de-differentiated cells were stimulated by ETX to a greater extent than were well-differentiated cells. None of the fibroblast lines tested significantly responded to ETX, regardless of the level of transformation of the fibroblast cell line (see Table II, below).

Although fibroblast cell lines do not respond to ETX, several normal and transformed fibroblast lines produce ETX. In contrast, conditioned medium from HepG2 cells, which migrate in response to ETX, contained no ETX activity. Thus, ETX, like SF/HGF, can act in a paracrine fashion (Stoker et al., supra, 1987). In this respect, ETX is distinct from most other motility factors, including AMF, MSF, autotaxin and SDMF, which are reported to operate in an autocrine fashion (Liotta et al., supra, 1986); Grey et al., 1989; Stracke et al., supra, 1992; Koyama et al., supra, 1993).

ETX can be useful for stimulating the migration of a tumor cell in vitro, wherein such stimulation indicates that migration of the tumor cell is dependent on ETX. For example, a tumor cell from a subject can be cultured in vitro. The migration of the tumor cell can be determined in the absence and in the presence of ETX. The detection of a tumor cell that shows increased migration in the presence of ETX can indicate that migration of the tumor cell is dependent on ETX. A subject having a tumor containing such cells can be a candidate for treatment using anti-ETX antibodies or an active fragment antagonist of ETX activity as described below. Thus, the present invention provides a method of determining whether a subject is a candidate for anti-ETX antibody therapy or therapy using an active fragment antagonist of ETX activity by detecting whether ETX stimulates migration of the subject's tumor cells in vitro. Stimulation of migration of the subject's tumor cells by ETX indicates the subject can be effectively treated using anti-ETX antibodies or an active fragment antagonist of ETX activity.

The responsiveness of a subject's tumor cells due to ETX also can be used to evaluate the prognosis of the subject following treatment by conventional means. For example, the migration of a subject's tumor cells in response to ETX can be determined prior to treatment. Following treatment of the subject using, for example, radiation therapy or chemotherapy, the responsiveness of the cells to ETX again can be determined. A decreased responsiveness of the tumor cells to ETX following treatment can indicate that the treatment has affected the invasiveness of the cells, thus providing a positive prognosis for the patient.

ETX also can be useful for increasing the sensitivity of a tumor cell to a cancer therapeutic agent. It is well known that various cancer therapeutic agents such as radiation or a chemotherapeutic agent such as a nucleoside analog, DNA intercalating agent or topoisomerase inhibitor are particularly effective in killing tumor cells that either are actively cycling through the cell cycle or are in a specific phase in the cell cycle. Often, however, the usefulness of a cancer therapeutic agent is limited because a relatively small proportion of the tumor cells are in the cell cycle or because the agent is equally toxic to normal cells.

ETX or a functional equivalent thereof can increase DNA synthesis in a tumor cell. Increased DNA synthesis indicates that a larger proportion of the tumor cells are traversing the cell cycle or that the cells are proceeding through the cell cycle at a faster rate. In either case, such tumor cells are more sensitive to a cancer therapeutic agent as described herein.

The present invention can be particularly useful in selectively increasing the sensitivity of a tumor cell to selective killing by a cancer therapeutic agent by contacting the tumor cell with ETX, which increases the level of DNA synthesis in the tumor cell, and a cancer therapeutic agent. Such contact can provide a therapeutic advantage because ETX can increase the level of DNA synthesis of the tumor cells but not of normal cells, thus selectively rendering the tumor cells but not the normal cells more sensitive to the cancer therapeutic agent.

As used herein, the term "increased sensitivity" means that the tumor cells can be killed by a lower dose of a cancer therapeutic agent due to the increased DNA synthesis occurring in the tumor cells as a result of contact with ETX. As used herein, the term "selective" means that the toxicity of a cancer therapeutic agent is increased preferentially against a tumor cell as compared to a normal cell due to the ability of ETX to increase DNA synthesis in the tumor cells but not in the normal cells.

ETX can increase DNA synthesis of a tumor cell in vitro, ex vivo or in vivo. When administered to a subject in vivo, ETX can be in the form of a pharmaceutical composition as described below. ETX also can be used to selectively increase the sensitivity of tumor cells, for example, in a bone marrow sample obtained from a subject, to a cancer therapeutic agent. In this case, a bone marrow sample, which can contain tumor cells, is removed from a subject and contacted ex vivo with ETX and with a cancer therapeutic agent. Such treatment can be useful for purging the subject's bone marrow of tumor cells prior to reintroducing the bone marrow into the subject following, for example, whole body irradiation cancer therapy.

The invention further provides antibodies that are specifically reactive with ETX. As used herein, the term "antibody" is used in its broadest sense to include polyclonal and monoclonal antibodies, as well as polypeptide fragments of antibodies that retain a specific binding activity for ETX of at least about $1 \times 10^5 M^{-1}$. One skilled in the art would know that anti-ETX antibody fragments such as Fab, F(ab')$_2$ and Fv fragments can retain specific binding activity for ETX and, thus, are included within the definition of an antibody. In addition, the term "antibody" as used herein includes naturally occurring antibodies as well as non-naturally occurring antibodies and fragments that retain binding activity. Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275–1281 (1989), which is incorporated herein by reference.

Particularly useful non-naturally occurring antibodies include chimeric antibodies and humanized antibodies. As used herein, the term "chimeric antibody" means an antibody having a human constant region and a variable region from an organism other than a human. For example, a chimeric antibody useful in the invention can consist of a human IgG constant region and a variable region obtained from a mouse anti-human ETX antibody. As used herein, the term "humanized antibody" means an antibody having human constant and framework regions and hypervariable regions from an organism other than a human. For example, a humanized antibody useful in the invention can consist of the amino acids that form the hypervariable region of a mouse anti-human ETX antibody and the amino acids that form the framework region and constant regions of a human IgG class antibody. Chimeric antibodies and humanized antibodies are particularly useful for administration to a human subject, since the likelihood of an immune response by the subject against the antibody is minimized.

Anti-ETX antibodies can be prepared using substantially purified ETX or an ETX fusion protein as an immunogen. In addition, an active fragment of ETX such as the amino acid sequence shown in FIG. 7 can be used as an immunogen. Methods for raising an antibody are routine and described, for example, by Harlow and Lane, *Antibodies: A laboratory manual* (Cold Spring Harbor Laboratory Press, 1988), which is incorporated herein by reference. One skilled in the art would know that ETX useful as an immunogen can be prepared from natural sources, as described herein, produced recombinantly or chemically synthesized. In some cases, a fragment of ETX, alone, may not be immunogenic. However, a non-immunogenic fragment or a synthetic peptide of ETX can be made immunogenic by coupling the hapten to a carrier molecule such bovine serum albumin or keyhole limpet hemocyanin. In addition, various other carrier molecules and methods for coupling a hapten to a carrier molecule are well known in the art (see, for example, Harlow and Lane, supra, 1988).

Polyclonal anti-ETX antibodies can be raised in rabbits. In addition, monoclonal antibodies can be obtained using known methods (Harlow and Lane, supra, 1988). Essentially, spleen cells from an ETX-immunized animal can be fused to an appropriate myeloma cell line such as SP/02 myeloma cells to produce hybridoma cells. Cloned hybridoma cell lines can be screened using labelled ETX polypeptide to identify clones that secrete anti-ETX monoclonal antibodies. Methods for labelling a polypeptide are well known (see below). Hybridomas that express antibodies having a desirable specificity and affinity can be isolated and utilized as a continuous source of monoclonal anti-ETX antibodies. Methods for identifying an anti-ETX antibody having an appropriate specificity and affinity and, therefore, useful in the invention also are known in the art and include, for example, enzyme-linked immunosorbent assays, radioimmunoassays and precipitin assays (Harlow and Lane, supra, 1988; chap. 14).

An anti-ETX antibody of the invention can be useful, for example, to purify ETX from a sample. For example, anti-ETX antibodies can be attached to a solid substrate such as a resin and can be used to affinity purify ETX. In addition, an anti-ETX antibody can be used to identify the presence of ETX in a sample. In this case, the anti-ETX antibody can be labelled so as to be detectable. An anti-ETX antibody can be detectably labelled using methods well known in the art (see, for example, Harlow and Lane, 1988; chap. 9). For example, an antibody can be labelled with any of various detectable moieties including a radiolabel, an enzyme, biotin or a fluorochrome. Following contact of a labelled antibody with a sample such as a tissue homogenate or a histological section of a tissue, specifically bound labelled antibody can be identified by detecting the particular moiety.

A labelled second antibody also can be used to identify specific binding of an unlabelled anti-ETX antibody. A second antibody generally will be specific for the particular class of the first antibody. For example, if an anti-ETX antibody is of the IgG class, a second antibody will be an anti-IgG antibody. Such second antibodies are readily available from commercial sources. The second antibody can be labelled using a detectable moiety as described above. When a sample is labelled using a second antibody, the sample is first contacted with a first antibody, then the sample is contacted with the labelled second antibody, which specifically binds to the first antibody and results in a labelled sample.

The invention also provides a method to reduce or inhibit the migration of a tumor cell by contacting the tumor cell with an anti-ETX antibody or with an active fragment of ETX that is an antagonist of ETX activity. As used herein, the terms "reduce" and "inhibit" have their common meanings. The terms are used together, here, to avoid any ambiguity as to the extent to which ETX acts. It is recognized, for example, that ETX can decrease the level of migration of a cell below a level that is detectable using a particular assay. In this situation, one would be unable to determine whether the rate of cell migration was reduced to a lower level or inhibited such that no migration was occurring. The use of these terms together precludes the need to distinguish these events.

As used herein, the term "contact" is used in its broadest sense to mean either direct contact of a tumor cell or indirect contact such as by contacting an environment containing the tumor cell with the anti-ETX antibody or the active fragment antagonist of ETX activity. As a result of such contact, tumor cell migration can be reduced or inhibited below the level of migration that occurred prior to the contact. An anti-ETX antibody can reduce or inhibit the migration of a tumor cell, for example, by sequestering ETX. An active fragment antagonist of ETX activity can act, for example, by binding to an ETX receptor on a cell, thereby preventing binding of ETX.

The disclosed method of reducing or inhibiting migration of a tumor cell can be useful in vitro or in vivo. The addition of an anti-ETX antibody or an active fragment of ETX that acts as an antagonist of ETX activity to tumor cells in vitro can be useful, for example, for determining the dependence of tumor cell migration on ETX. The ability of the anti-ETX antibody or the active fragment antagonist of ETX activity to reduce or inhibit the migration of tumor cells in vitro can indicate that the antibody can be useful to reduce or inhibit the migration of the same tumor cells in a subject. Thus, the invention provides an in vitro screening assay to determine whether an anti-ETX antibody or an active fragment antagonist or ETX activity can be useful for treating a subject having a tumor.

An anti-ETX antibody or active fragment antagonist of ETX activity is particularly useful when administered to a subject having a tumor cell. ETX can be involved in the invasion and metastasis of tumor cells. The increased motility of malignant tumor cells likely is a crucial factor in invasion and metastasis (see Hart et al., supra, 1989, and Liotta and Stetler-Stevenson, supra, 1991). Since ETX is produced by mesenchymal cells such as fibroblasts, tumor cells can be stimulated to invade into the connective tissue beneath the basement membrane of a tissue. In addition, a paracrine motility factor such as ETX can be produced by stromal cells present in the tumor and can enhance the dissociation of tumor cells from primary lesion. The administration of an anti-ETX antibody to a subject having a tumor can result in sequestration of ETX by the antibody, resulting in a decreased level of ETX available for stimulating migration of the tumor cells in the subject. The administration of an active fragment of ETX that can act as an antagonist to ETX activity to a subject having a tumor can result, for example, in competition with an ETX receptor on a cell. In this case, the decreased availability of ETX receptors for binding ETX results in decreased ETX binding to a cell, which can reduce or inhibit the stimulation of tumor cell migration in the subject.

An anti-ETX antibody or an active fragment antagonist of ETX activity also can be useful for inhibiting DNA synthesis in a tumor cell, including a tumor of epithelial origin. As disclosed herein, ETX increases DNA synthesis in such a tumor cell. Thus, ETX can be an essential factor for DNA synthesis in these cells and, therefore, for cell proliferation. The present invention provides a method of reducing or inhibiting proliferation of a tumor cell by contacting the tumor cell with an anti-ETX antibody or an active fragment antagonist of ETX activity. Such contact can prevent ETX from effecting its function of increasing DNA synthesis in the tumor cell and, therefore, can reduce or inhibit tumor cell proliferation.

When administered to a subject, the compositions of the invention are particularly useful when administered as a pharmaceutical composition containing, for example, ETX, an anti-ETX antibody or an active fragment antagonist of ETX activity and a pharmaceutically acceptable carrier. Pharmaceutically acceptable carriers are well known in the art and include, for example, aqueous solutions such as physiologically buffered saline or other solvents or vehicles such as glycols, glycerol, oils such as olive oil or injectable organic esters.

A pharmaceutically acceptable carrier can contain physiologically acceptable compounds that act, for example, to stabilize or to increase the absorption of ETX, an anti-ETX antibody or an active fragment antagonist of ETX activity. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. The pharmaceutical composition also can contain an agent such as a cancer therapeutic agent.

One skilled in the art would know that a pharmaceutical composition containing ETX, an anti-ETX antibody or an active fragment antagonist of ETX activity can be administered to a subject having a tumor by various routes including, for example, orally or parenterally, such as intravenously, intramuscularly, subcutaneously or intraperitoneally. The composition can be administered by injection or by intubation. The pharmaceutical composition also can be incorporated, if desired, into liposomes or microspheres or can be microencapsulated in other polymer matrices (Gregoriadis, *Liposome Technology*, Vol. 1 (CRC Press, Boca Raton, Fla. 1984), which is incorporated herein by reference). Liposomes, for example, which consist of phospholipids or other lipids, are nontoxic, physiologically acceptable and metabolizable carriers that are relatively simple to make and administer.

In order to reduce or inhibit tumor cell migration, an anti-ETX antibody or an active fragment antagonist of ETX activity must be administered in an effective dose, which is about 0.01 to 100 mg/kg body weight. Similarly, an effective dose of ETX must be administered to a subject in order to increase the level of DNA synthesis in the subject's tumor cells and, thereby, render the tumor cells more sensitive to killing by a cancer therapeutic agent. As used herein, the term "effective dose" means the dose of an anti-ETX antibody or an active fragment antagonist of ETX that can reduce or inhibit tumor cell migration in a subject or the dose of ETX that can increase the level of DNA synthesis in the subject's tumor cells. An effective dose can be determined using methods known to those in the art.

The total effective dose can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of ETX, an anti-ETX antibody or an active fragment antagonist of ETX activity required to obtain an effective dose in a subject depends on many factors including the age and general health of the subject as well as the route of administration and the number of treatments to be administered. In view of these factors, the skilled artisan would adjust the particular dose so as to obtain an effective dose for reducing or inhibiting tumor cell migration in the subject or for increasing DNA synthesis in the tumor cells.

Since the migration of a tumor cell in a subject can be reduced or inhibited by contacting the tumor cell with an anti-ETX antibody or an active fragment antagonist of ETX activity, such administration can reduce the likelihood of tumor cell invasion or metastasis in the subject. In addition, since the administration of ETX to a subject can increase the level of DNA synthesis in the subject's tumor cells, such administration can render the tumor cells more sensitive to killing by a cancer therapeutic agent.

The following examples are intended to illustrate but not limit the invention.

EXAMPLE I

Identification of Epitaxin Activity

This example describes a method for identifying ETX activity in fibroblast conditioned medium.

Unless indicated otherwise, cells were grown in α-modified minimal essential medium (α-MEM; Gibco; Gaithersburg, Md.) supplemented with 9% fetal calf serum (FCS) and 2 mM glutamine and containing 100 units/ml penicillin and 100 μg/ml streptomycin ("maintenance medium"). Human hepatocellular carcinoma cells (HepG2), canine kidney epithelial cells (MDCK), human lung adenocarcinoma cells (A549), human breast ductal carcinoma cells (ZR-75-1) and rat bladder carcinoma cells (NBT-II) are available from the American Type Culture Collection and were cultured in maintenance medium, except that ZR-75-1 cells were cultured in RPMI-1640, which was supplemented as described for maintenance medium.

Chemically-transformed human fibroblast cell lines HuT-12, HuT-14 and HuT-14T, which were derived from human normal fibroblast KB cells (Kakunaga, *Proc. Natl. Acad. Sci., USA* 75:1334–1338 (1978)), are described by Leavitt et al., *Cell* 28:259–268 (1982), each of which is incorporated herein by reference). The rat hepatoma cell lines, H4II, Fao and C2, which are described by Ott et al., *EMBO J.* 3:2505–2510 (1984), and by Pitot et al., *Natl. Canc. Inst. Monogr.* 13:229–242 (1964), each of which is incorporated herein by reference, were cultured in 1:1 mixture of NCTC 135 (Sigma) and Ham F12 (Gibco) media supplemented with 5% FCS, 2 mM glutamine and antibiotics.

Conditioned medium was obtained by growing cells to confluency, washing the cells extensively with α-MEM, then culturing the cells in α-MEM supplemented with 2 mM glutamine and antibiotics ("serum-free medium") for 2 days. The serum-free conditioned medium was collected, filtered to remove cells and supplemented with 5 mM EDTA and 0.2 mM phenylmethylsulfonylfluoride. Conditioned medium was stored at −20° C. In initial experiments, conditioned media from two human embryonic lung fibroblast cell lines, IMR-90 and WI-38, a chemically transformed human fibroblast line, HuT-12, and HepG2 cells were examined for cell migratory activity using the modified Boyden chamber assay.

The cell migration assay was performed using a modified Boyden chamber assay in a 48 well chemotaxis apparatus (Neuroprobe, Cabin John, MD) as described by Stracke et al., Biochem. Biophys. Res. Comm. 153:1076–1083 (1988), which is incorporated herein by reference. Polycarbonate filters with 8 μm pores (Poretics Corp.; Livermore, Calif.) were coated with 100 μg/ml type I collagen (Collagen Corp.; Palo Alto, Calif.) diluted in 20 mM acetic acid, washed with phosphate buffered saline (PBS), then with water and placed on lower chambers of the chemotaxis apparatus, which contained the conditioned medium sample.

Prior to each assay, cells were collected by trypsinization, then washed and incubated in maintenance medium for 2 hr to allow the cells to recover. Following the 2 hr recovery period, cells were washed with α-MEM containing 1 mg/ml BSA (α-MEM/BSA) and $5 \times 10^4$ cells were suspended in 40 μl α-MEM/BSA and added to each upper chamber. The cells were incubated for 5 hr, then the filter was removed from the apparatus, fixed with methanol and stained with Diff-Quick (Baxter; Miami, Fla.). The number of cells on the lower surface of the filter was counted in four randomly chosen fields at 200× magnification). Using this assay, conditioned media obtained from the human embryonic lung fibroblast cell lines, IMR-90 and WI-38, and the chemically transformed human fibroblast line, HUT-12, stimulated the migration of HepG2 cells, whereas conditioned medium from HepG2 cells does not contain such an activity (not shown).

In order to determine whether the motility stimulating activity was due to a known cytokine, various cytokines were tested using the cell migration assay. Recombinant acidic FGF, basic FGF, PDGF (AA form), IL-6, interferon-τ, IGF-1 were purchased from Boehringer Mannheim (Indianapolis, Ind.). Human TGF-β1, porcine TGF-β2 and recombinant human TNF-α were purchased from R & D Systems (Minneapolis, Minn.). Recombinant human hepatocyte growth factor (HGF; SF/HGF; Nakamura et al., Nature 342:440–443 (1989), which is incorporated herein by reference). Human autotaxin (Stracke et al., supra, 1992).

Figure 3:
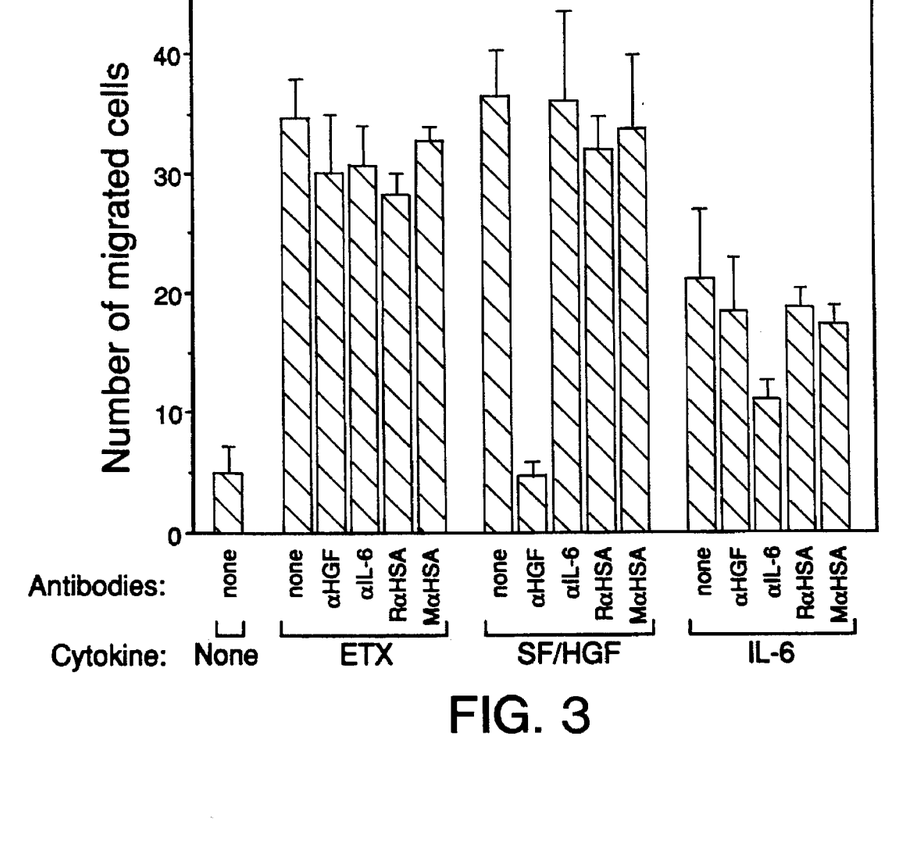

Only SF/HGF and IL-6 induced significant migration of HepG2 cells in the cell migration assay (FIG. 3). As shown, IL-6 slightly stimulated the migration of HepG2 cells and SF/HGF showed a strong activity. However, HuT-12 conditioned medium had little effect on MDCK cells in the scatter assay (not shown), suggesting that the activity in the conditioned media of these cells was distinct from SF/HGF (not shown). Based on these results, HuT-12 cells were used as the source of conditioned media for the isolation of ETX.

EXAMPLE II

Purification of Epitaxin

This example describes the methods used to purify and characterize ETX.

Epitaxin was purified from ten liters of HuT-12 cell conditioned medium. The serum-free conditioned medium was precipitated by adjusting the medium to 40% saturation of ammonium sulfate. The precipitate was removed by centrifugation at 8000 rpm in a Sorvall GSA rotor and both the supernatant and the precipitate were tested from ETX activity using the cell migration assay described above. Both fractions contained activities that induced motility of HepG2 cells. However, the activities in the precipitate were due to haptotaxis caused by the presence of adhesion proteins such as fibronectin and laminin (not shown).

The supernatant fraction (16.7 liters), which contained the ETX activity, was concentrated to a volume of 1000 ml by ultrafiltration using a 30 kDa cut-off membrane (PTTK Minitan plate; Millipore; Bedford, Mass.). Aggregates were removed by centrifugation and the concentrate was applied to a phenyl-Sepharose column (2.5×17 cm; Pharmacia; Piscataway, N.J.) that was preequilibrated with 50 mM Tris/HCl containing 1.6M ammonium sulfate. The column was eluted using simultaneous linear gradients of increasing ethylene glycol (0–50%) and decreasing ammonium sulfate (1.6–0M) in 50 mM Tris/HCl (pH 7.5).

Active fractions were identified using the cell migration assay. Samples for bioassay were prepared by lyophilizing an aliquot of each fraction in the presence of BSA (Fraction V; Sigma) using a Speed-Vac (Savant; Farmingdale, N.Y.). The lyophilized sample was dissolved in serum-free medium and the amount of BSA was adjusted to a final concentration of 1 mg/ml.

The active fractions from the phenyl-Sepharose column were combined, then fractionated by a series of RP-HPLC using Vydac C4 columns (4.6×250 mm; Separations Group; Hesperia, Calif.) on a Shimadzu LC-600 HPLC system. Eluates were monitored by absorbance at 210 nm and 1 ml fractions were collected. The combined active fraction was loaded onto a Vydac C4 column (4.6×250 mm) preequilibrated with 0.1% trifluoroacetic acid (TFA) and eluted by a linear gradient of 10–60% acetonitrile. The recovery of activity in this step was low (~13%) due, in part, to the denaturing solvent used for the RP-HPLC. In a separate experiment, exposure of the active fraction obtained from phenyl-Sepharose to 0.1% TFA for 1 hour reduced the activity to less than 25% of the original activity.

Despite the loss of activity following the first RP-HPLC, a peak of activity was detected in the fractions eluted with 29% acetonitrile (FIG. 1.A.). The active fraction was reapplied to the C4 column and eluted with a 16–36% linear gradient of acetonitrile. The activity again eluted at a concentration of about 29% acetonitrile (FIG. 1.B.).

The active fraction following the second RP-HPLC was concentrated by lyophilization and proteins were resolved by SDS-PAGE in a 4–20% gel (Novex; San Diego, Calif.) under nonreducing conditions. SDS-PAGE revealed a single band at 36 kDa on a silver stained gel in the active fractions. The density of the band correlated with the migration stimulating activity across the elution profile (compare FIGS. 1.B. and 1.C.).

Using the above procedure, ETX activity was purified 1038-fold relative to the supernatant of the ammonium sulfate precipitates (Table I). Since the original conditioned medium contained substantial amounts

TABLE I

PURIFICATION OF EPITAXIN

| Purification Step | Protein (mg) | Total activity§ (units) | Specific Activity (units/μg) |
|---|---|---|---|
| HuT-12 conditioned medium | 715≠ | —* | —* |
| 40% (NH$_4$)$_2$SO$_4$ supernatants | 338≠ | 87,900 | 0.26 |
| Phenyl-Sepharose | 18≠ | 70,300 | 3.9 |
| Vydac C4 #1 | 0.723# | 9,300 | 12.9 |
| Vydac C4 #2 | 0.020# | 5,400 | 270 |

≠Protein was determined by the BCA assay kit (Pierce, Rockford, IL).
Protein was estimated by comparing the density of silver-stained bands with standard proteins on the SDS-gel.
§One unit of activity was defined as half maximal stimulation of HepG2 cell migration induced by the active fraction from phenyl-Sepharose chromatography.
*Activities in the original conditioned medium could not be determined due to the contaminating haptotactic activities derived from adhesion proteins present in the conditioned medium.

of fibronectin and laminin, which stimulated migration of the HepG2 cells, the total purification from the conditioned medium could not be determined.

In order to confirm that the 36 kDa polypeptide identified by SDS-PAGE is responsible for the migration stimulating activity, the active fractions from the second RP-HPLC were resolved by SDS-PAGE as described above, then electrophoretically transferred to a PVDF membrane (Novex). Following transfer, the membrane was cut along its length into 12 pieces and the proteins present on each piece were eluted by incubation with 40% acetonitrile at 37° C. for 3 hr, then with 40% acetonitrile/0.05% TFA at 50° C. for 30 min (Stone et al., In *A Practical Guide to Protein and Peptide Purification for Microsequencing* (Academic Press 1989), which is incorporated herein by reference.

Figure 2A:
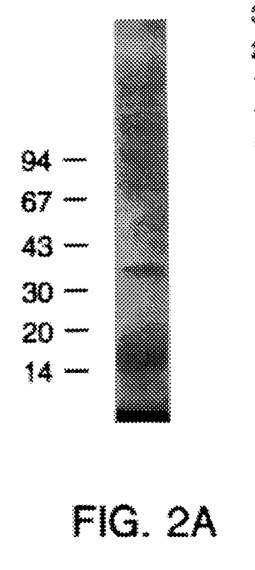
Figure 2B:
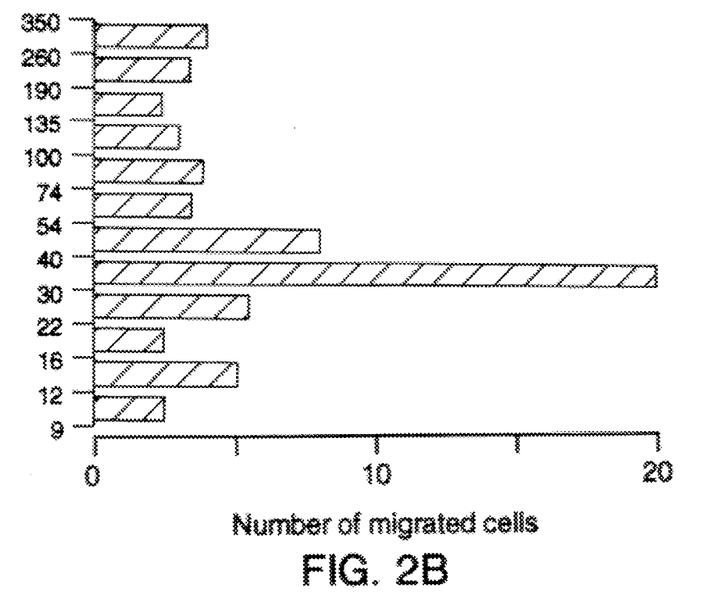

The eluates from each filter piece were combined, lyophilized in the presence of 100 μg BSA, dissolved in 100 μl of α-MEM and assayed for ETX activity. As shown in FIG. 2, the HepG2 migration inducing activity was detected in the slice corresponding to a molecular mass of 30 to 40 kDa, which contains the 36 kDa polypeptide (FIG. 2). This result confirms that the 36 kDa band on the SDS-PAGE represents substantially purified ETX.

EXAMPLE III

Characterization of Epitaxin

This example describes methods for characterizing the structure and activity of ETX.

As described above, of the tested cell motility factors, only SF/HGF and IL-6 significantly stimulated the migration of HepG2 cells. Although SF/HGF and IL-6 had migration stimulating activities, the apparent molecular masses of these cytokines indicated that ETX is a distinct cell motility factor. This was confirmed by examining the effects of goat anti-human SF/HGF neutralizing antibodies (R & D Systems; Minneapolis, Minn.) and mouse monoclonal anti-human IL-6 neutralizing antibodies (Biosource International; Camarillo, Calif.) on the ETX-stimulated migration of HepG2 cells. As shown in FIG. 3, the neutralizing SF/HGF and IL-6 antibodies inhibited migration stimulated by the respective cytokines, but not by ETX. These results indicate that ETX is distinct from SF/HGF and IL-6.

Figure 4:
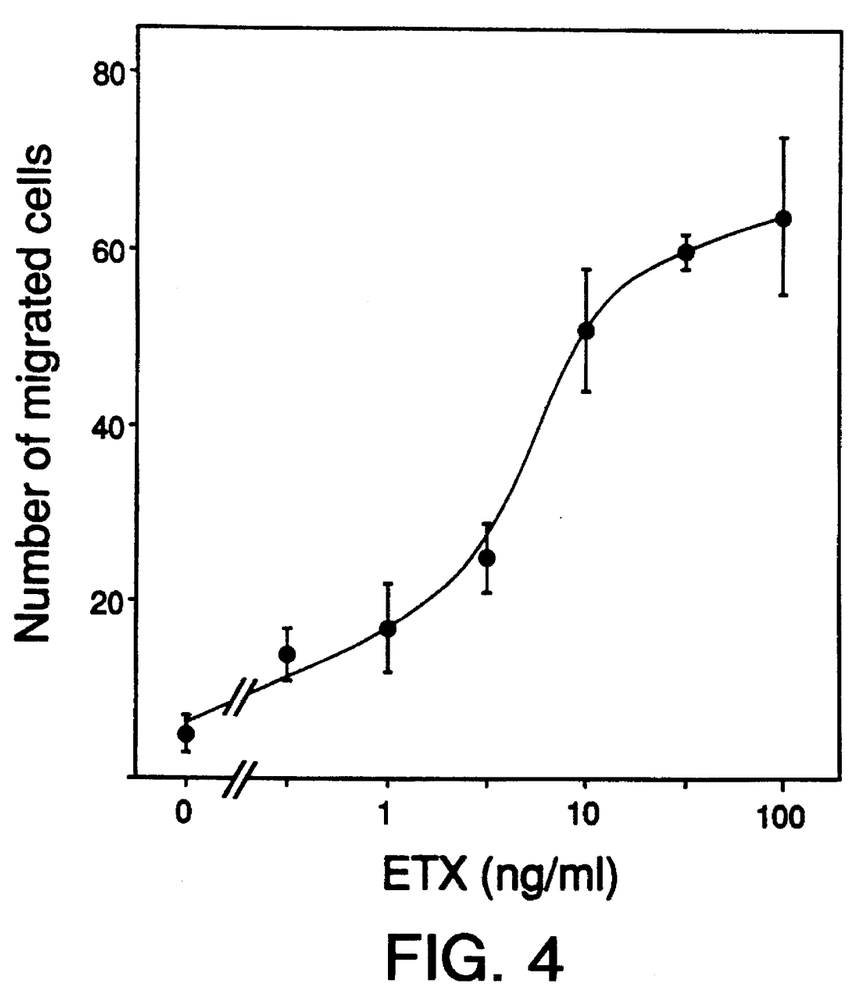
FIG. 4. Dose-dependent Effect of Epitaxin on the Migration of HepG2 Cells. Purified ETX was lyophilized in the presence of BSA, dissolved in serum-free medium and assayed for the activity to stimulate the migration of HepG2 cells. Data represent the mean ±1 SD (n=3).

Analysis of the dose-response effect of ETX on HepG2 cell migration revealed that ETX is active in a concentration above 1 ng/ml and that half maximal activity occurs at 4.2 ng/ml (FIG. 4). This estimate does not account for the approximately 10-fold loss of ETX activity caused by exposure to 0.1% TFA during RP-HPLC. Thus, ETX can have substantially greater activity under physiologic conditions.

In order to determine whether ETX-induced motility was chemotactic (directed motility) or chemokinetic (random motility), a checkerboard analysis was performed as described by Zigmund and Hirsch, *J. Exp. Med.* 137:387–410 (1973) and by Stracke et al., *J. Biol. Chem.* 267:2524–2529 (1992), each of which is incorporated herein by reference. Briefly, 5×10$^3$ cells suspended in 100 μl of maintenance medium were added to each well of a standard 96 well tissue culture plate. Each well contained 100 μl serum-free medium containing ETX. The cells were incubated for 18 hr, then were fixed, stained with Diff-Quick and analyzed for penetration to the lower side of the membrane.

Figure 5:
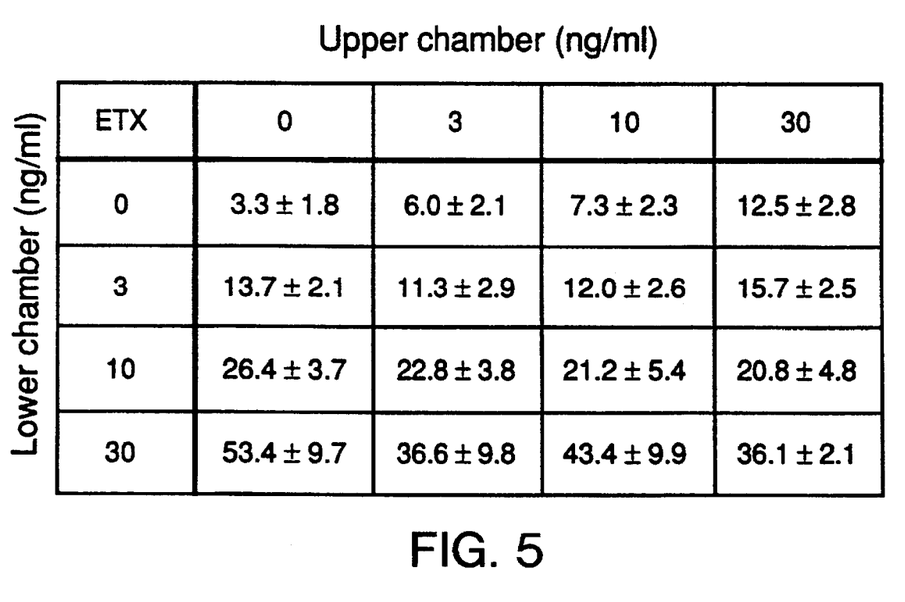
FIG. 5. Checkerboard Analysis of the Motility of HepG2 Cells Stimulated by Epitaxin. Varying concentrations of ETX (0 to 30 ng/ml) were added to the upper and lower chambers of the 48 well chemotaxis 5 apparatus to create different sets of concentration gradients and the number of migrating HepG2 cell was counted. Data represent the mean ±1 SD for each point in the checkerboard (n=3).
Figure 6:
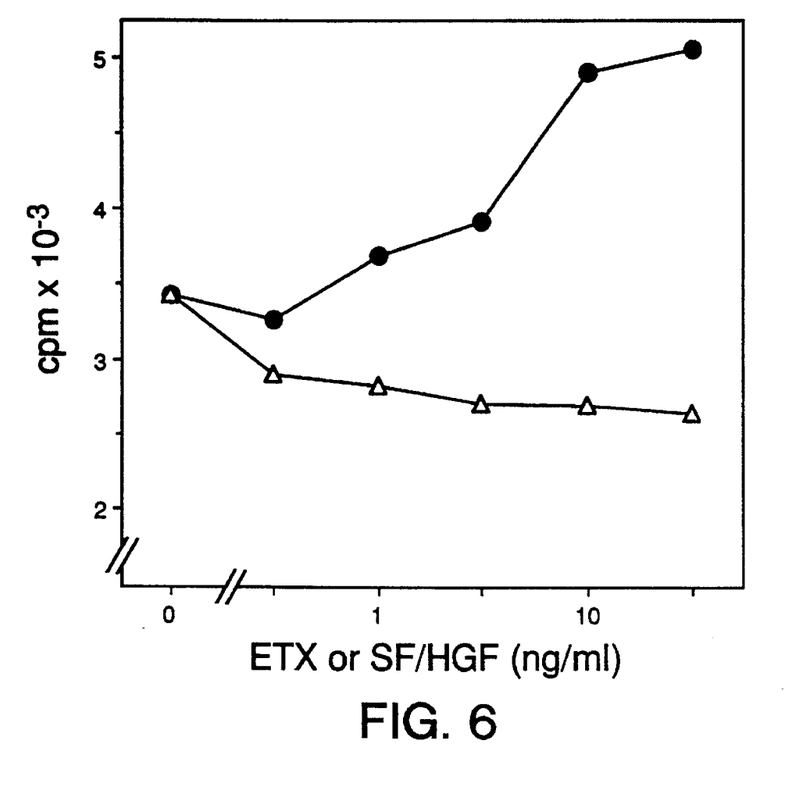

The results of this analysis demonstrated that ETX stimulates both chemotactic and chemokinetic responses (FIG. 5). At 30 ng/ml, the chemotactic response was 16× above background and the chemokinetic response was 11× above background. Such a mixed response is similar to that induced by autotaxin, SF/HGF and insulin (Stracke et al., supra, 1988; Stoker, *J. Cell. Physiol.* 139:565–569 (1989); Stracke et al., supra, 1992). In contrast, IGF-1 is almost entirely chemotactic (Stracke et al., supra, 1988).

Like epitaxin, SF/HGF stimulates the migration of HepG2 cells (see FIG. 3). However, SF/HGF also can cause colonies of various cell lines, including HepG2 and MDCK cells, to scatter (Stoker et al., *Nature* 327:239–242 (1987), which is incorporated herein by reference; Weidner et al., supra, 1991; Tajima et al., *Exp. Cell Res.* 202:423–431 (1992)). To confirm that ETX and SF/HGF have distinct effects on HepG2 cells, ETX and SF/HGF were compared using the scatter assay. SF/HGF scattered both HepG2 and MDCK cells, as reported by Tajima et al., supra (1992), whereas ETX did not cause any discernible morphological changes in either cell type (not shown). These results indicate that, while ETX and SF/HGF both stimulate the motility of HepG2 cells, these cell motility factors act by different mechanisms.

The effect of ETX on cell proliferation was examined by $^3$H-thymidine incorporation assays. The assays were performed as described by Yamaguchi et al., *Nature* 346:281–284 (1990), which is incorporated herein by reference, except that the assay was performed in Corning 96-½ multiwell plates (0.16 cm$^2$ culture surface per well; Corning, N.Y.). ETX stimulated DNA synthesis of HepG2 cells by about 50%. In contrast, SF/HGF inhibited growth of HepG2 cell by about 25%. The growth inhibitory activity of SF/HGF has previously been reported (Shiota et al., *Proc. Natl. Acad. Sci. USA* 89:373–377 (1992); Tajima et al., supra, 1992)). This result further indicates that ETX and SF/HGF are distinct factors.

The target cell specificity of ETX was determined by using the cell migration assay to examine the ability of ETX to stimulate migration of different cell types, including a series of rat hepatoma cell lines and various epithelial and fibroblast cell lines. The hepatoma cell lines, H4II, Fao, and C2, are derived from Reuber hepatoma H35 (Ott et al., *EMBO J.* 3:2505–2510 (1984)). H4II and Fao are clonal cell lines that have well-differentiated phenotypes and express a variety of liver-specific genes. C2 is an Fao-derived clone that has a de-differentiated phenotype and lacks expression of liver-specific genes including albumin (Ott et al., supra, 1984).

As shown in Table II, the well-differentiated H4II cells did not respond to ETX, whereas the de-differentiated C2 cells were stimulated to a greater extent than HepG2 cells. Although the motility of H4II and Fao cells was stimulated by ETX, the magnitude of the response was less than that of C2 cells. These results indicate that the responsiveness of the hepatoma cells toward ETX is inversely correlated with the stage of differentiation of the cells.

The ability of ETX to stimulate migration of several tumor cell lines of epithelial origin, including MDCK cells, human breast ductal carcinoma ZR-75-1 cells, human lung adenocarcinoma A549 cells and rat bladder tumor NBT-II cells also was examined. MDCK cells are derived from normal kidney epithelium and retain a highly differentiated phenotype; the other cell lines are derived from tumors. ETX stimulated the migration of each of the tumor-derived cell lines, but not the MDCK cells (Table II). This result is consistent with the results obtained for the hepatoma cells. Thus, highly differentiated cells are less responsive to ETX than are less differentiated cells.

TABLE II

EFFECT OF EPITAXIN ON VARIOUS CELL LINES

| Cell line | Cytokine | Number of cells migrated at*: | |
|---|---|---|---|
| | | 0 ng/ml | 30 ng/ml |
| Rat hepatoma lines | | | |
| H4II | epitaxin | 0 | 13.0 ± 2.2 |
| Fao | epitaxin | 0 | 10.7 ± 1.2 |
| C2 | epitaxin | 8.3 ± 1.3 | 224.3 ± 11.3 |
| Epithelial lines | | | |
| MDCK | epitaxin | 0 | 0 |
| MDCK | SF/HGF | 0 | 36.3 ± 8.5 |
| ZR-75-1 | epitaxin | 0 | 23.8 ± 2.0 |
| ZR-75-1 | IL-6 | 0 | 0 |
| A549 | epitaxin | 53.0 ± 10.2 | 182.8 ± 17.2 |
| NBT-II | epitaxin | 19.8 ± 6.2 | 279.3 ± 25.5 |
| Fibroblast lines | | | |
| HuT-12 | epitaxin | 118.4 ± 22.0 | 127.2 ± 14.3 |
| HuT-14 | epitaxin | 39.6 ± 6.5 | 38.0 ± 6.2 |
| HuT-14T | epitaxin | 90.6 ± 15.5 | 83.1 ± 7.3 |

*The migration assay was performed as described in Materials and Methods with the cell lines indicated in the table. Suspensions of $5 \times 10^4$ cells in serum-free media containing 1 mg/ml Of BSA were added to each well and incubated for 5 hours except for H4II and Fao cells which were incubated for 18 hours. Data represent the mean ± 1 SD (n = 3).

The migration of the MDCK cells was not stimulated by ETX at concentrations as high as 100 ng/ml. In contrast, SF/HGF stimulated the migration of MDCK cells in the concentration range of 10–30 ng/ml (Table II), which is consistent with a published report (Stoker et al., supra, 1987). ZR-75-1 cells have been shown to respond to IL-6 by cell scattering (Tamm et al., supra, 1989). In the Boyden chamber assay, however, IL-6 did not stimulate the migration of ZR-75-1 cells, whereas ETX did stimulate migration of these cells.

The responsiveness of a series of human fibroblast lines having different levels of tumorigenicity also has been examined. HuT-12, HuT-14 and HuT-14T are chemically transformed human fibroblasts that originated from common ancestor cells (Kakunaga, supra, 1978). HuT-12 cells are non-tumorigenic in the nude mouse assay, whereas HuT-14 is tumorigenic and HuT-14T is highly tumorigenic (Leavitt et al., Cell 28:259–268 (1982), which is incorporated herein by reference). Each of these cell lines showed significant levels of unstimulated motility. However, the level of motility was not enhanced by ETX (Table II).

Figure 7:
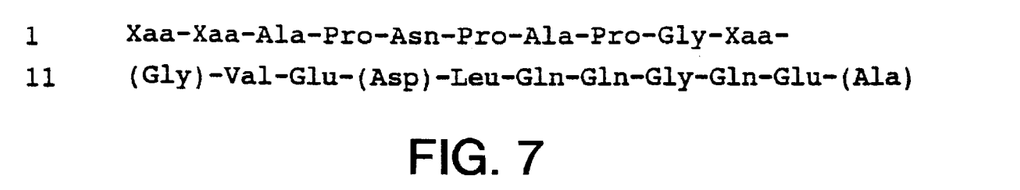
FIG. 7. Partial Amino Acid Sequence of Epitaxin. The N-terminal amino acids of ETX were determined by microsequencing analysis (SEQ ID NO:1). Each amino acid is indicated by its three letter code. "Xaa" indicates amino acid residues that could not be determined unambiguously. Amino acids shown in parentheses indicate the most likely residue at the position. Numbers to the left indicate the amino acid number.

The partial amino acid sequence of ETX was determined using microsequencing analysis. Two µg purified protein was sequenced using an Applied Biosystems (Foster City Calif.) Model 470A protein sequencer as described by Esch, Anal. Biochem. 136:39–47 (1984), which is incorporated herein by reference. Released phenylthiohydantoin (PTH) amino acids were analyzed by an on-line Applied Biosystems Model 120A PTH-amino acid analyzer. The N-terminal amino acid sequence is shown in FIG. 7 (SEQ ID NO:1 ). This twenty amino acid sequence has no significant homology to any proteins listed in Brookhaven Protein DataBank and GenBank.

These results indicate that ETX is different from other cell motility factors based on its amino acid sequence, apparent molecular mass, effect on DNA synthesis and target cell specificity. Thus, ETX is a novel tumor cell motility factor that can induce migration, for example, of tumor cells of epithelial origin and is produced by fibroblasts.

Although the invention has been described with reference to the examples above, it should be understood that various modifications can be made without departing from the spirit of the invention. Accordingly, the invention is limited only by the following claims.

We claim:

1. A substantially purified polypeptide having epitaxin activity, said polypeptide having an apparent molecular mass of about 36 kiloDalton and comprising an N-terminal amino acid sequence as shown in FIG. 7 (SEQ ID NO:1).

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 21 amino acids
        ( B ) TYPE: amino acid
        ( D ) TOPOLOGY: linear     ( i x ) FEATURE:
        ( A ) NAME/KEY: Peptide
        ( B ) LOCATION: 1
        ( D ) OTHER INFORMATION: /note= "Xaa indicates an amino acid
           residue that could not be determined
           unambiguously."

( i x ) FEATURE:
    ( A ) NAME/KEY: Peptide
    ( B ) LOCATION: 2
    ( D ) OTHER INFORMATION: /note= "Xaa indicates an amino acid residue that could not be determined unambiguously."

( i x ) FEATURE:
    ( A ) NAME/KEY: Peptide
    ( B ) LOCATION: 10
    ( D ) OTHER INFORMATION: /note= "Xaa indicates an amino acid residue that could not be determined unambiguously."

( i x ) FEATURE:
    ( A ) NAME/KEY: Peptide
    ( B ) LOCATION: 11
    ( D ) OTHER INFORMATION: /note= "Xaa indicates that Gly is the most likely residue at this position."

( i x ) FEATURE:
    ( A ) NAME/KEY: Peptide
    ( B ) LOCATION: 14
    ( D ) OTHER INFORMATION: /note= "Xaa indicates that Asp is the most likely residue at this position."

( i x ) FEATURE:
    ( A ) NAME/KEY: Peptide
    ( B ) LOCATION: 21
    ( D ) OTHER INFORMATION: /note= "Xaa indicates that Ala is the most likely residue at this position."

( x i ) SEQUENCE DESCRIPTION: SEQ ID NO:1:

```
Xaa  Xaa  Ala  Pro  Asn  Pro  Ala  Pro  Gly  Xaa  Xaa  Val  Glu  Xaa  Leu  Gln
1                  5                            10                       15

Gln  Gly  Gln  Glu  Xaa
                20
```